United States Patent [19]
Adler, Sr. et al.

[11] 4,276,253
[45] Jun. 30, 1981

[54] METHOD FOR HISTOLOGY SPECIMEN LABELLING

[75] Inventors: Stanford L. Adler, Sr., New Milford, Conn.; Abraham Gordon, Teaneck, N.J.; Leonard Ornstein, White Plains, N.Y.

[73] Assignee: Technicon Instruments Corporation, Tarrytown, N.Y.

[21] Appl. No.: 31,714

[22] Filed: Apr. 20, 1979

[51] Int. Cl.³ .................. B29C 6/02; B29C 9/00
[52] U.S. Cl. .................. 264/247; 83/915.5; 264/78; 264/158; 264/250; 264/277
[58] Field of Search .............. 428/13; 425/117; 40/2 C; 83/915.5; 128/749, 751; 264/78, 158, 250, 277, 247

[56] References Cited

U.S. PATENT DOCUMENTS

| | | | |
|---|---|---|---|
| 56,068 | 7/1866 | Lincoln | 40/2 C |
| 304,913 | 9/1884 | Craig | 264/250 |
| 1,994,164 | 3/1935 | Bailey . | |
| 2,614,454 | 10/1952 | Steffen . | |
| 3,613,265 | 10/1971 | Stern et al. | 264/277 |
| 3,674,396 | 7/1972 | McCormick | 425/117 |
| 3,700,533 | 10/1972 | Schmitz | 264/158 |
| 3,996,326 | 12/1976 | Schachet | 264/158 |
| 4,116,439 | 9/1978 | Chavarria et al. | 264/250 |

Primary Examiner—James B. Lowe
Attorney, Agent, or Firm—S. P. Tedesco

[57] ABSTRACT

A method for labelling a histological specimen, wherein such specimen is embedded in a paraffin block along with an integral set of supported elongated elements identifying such specimen for subsequent sectioning on a microtome. The identification elements are sectioned concurrently with the specimen, so as to form an integral part of the section.

7 Claims, 12 Drawing Figures

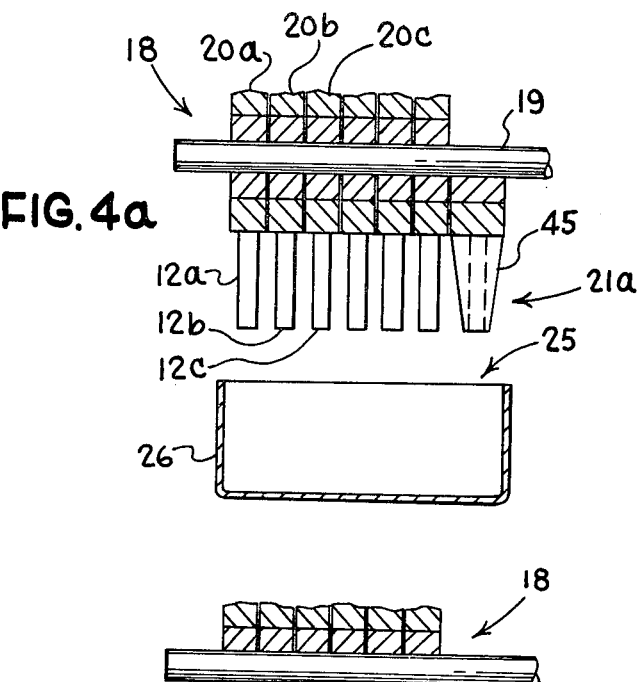
FIG.4a
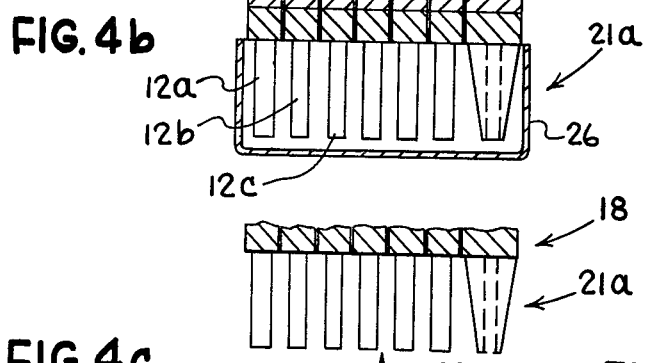
FIG.4b
FIG.4c
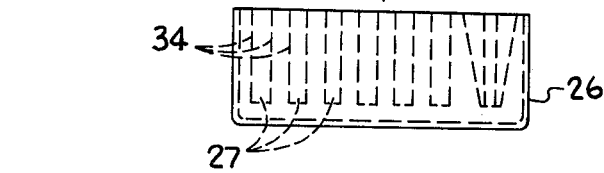
FIG.4d
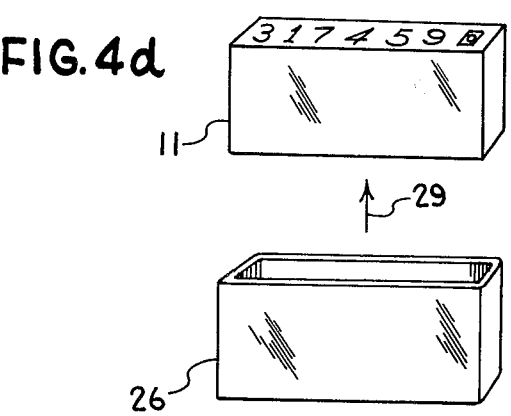
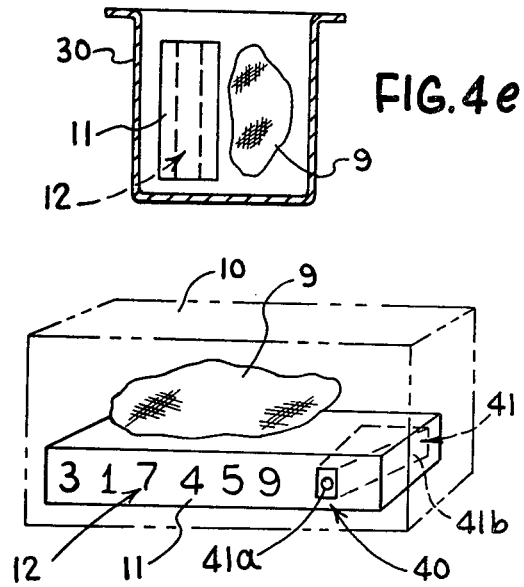
FIG.4e
FIG.4f
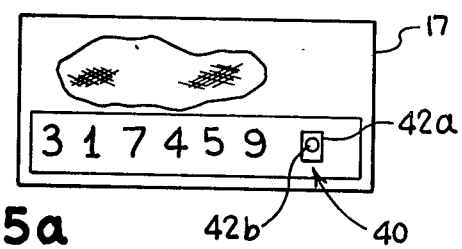
FIG.5a
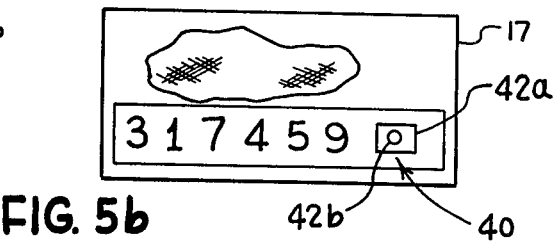
FIG.5b
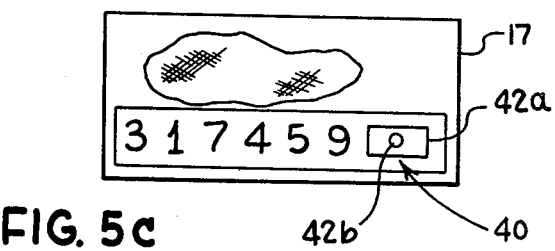
FIG.5c

METHOD FOR HISTOLOGY SPECIMEN LABELLING

FIELD OF THE INVENTION

The invention pertains to a method for positive labelling of histological tissue specimens and, more particularly, to the identical labelling of a plurality of sections cut from a single specimen.

BACKGROUND OF THE INVENTION

To prepare a section of a biological specimen, such as a histological tissue specimen, for mounting upon a microscope slide, typically after fixation, dehydration and infiltration with melted paraffin, the specimen is embedded in a block of paraffin. Typically, sections are then cut from the embedded specimen by mounting the block of paraffin in the vise of a microtome, and relatively moving a cutting blade through the block, following small incremental advances at right angles to the cutting motion.

The sections are then mounted upon one or more microscopic slides and stained. Apparatus and procedures for mounting tissues upon microscope slides are generally described in the patent to: J. B. McCormick, Embedding Structure and Method, U.S. Pat. No. 2,996,762, issued on Aug. 22, 1971.

One of the long standing problems with the preparation of such slides resides in assuring proper identification of each tissue specimen throughout the entire tissue processing. Presently, each specimen comes to the laboratory with an accompanying handwritten paper label, typically bearing the patient's identification number. Throughout the processing, this label is manually transferred or transcribed several times to various processing containers. After processing, each slide is hand-marked with the label number by the technician. Such procedure is fraught with opportunity for error, and is time-consuming. The invention addresses itself to the above problem. The invention provides a method and apparatus for conveniently and accurately labelling each section with an identification number. This identification number, which becomes an integral part of each tissue section, accompanies the specimen from the very outset of its processing through to the making of the finished slides, wherein the number becomes an integral part of each tissue section.

SUMMARY OF THE INVENTION

This invention relates to the labelling of a histological specimen. The specimen is co-embedded within an embedding medium with a plurality of elongated elements, which serve to identify the specimen. In the direction of elongation, the elements are embedded at least as deep as the specimen perpendicular to the intended sectioning plane of the embedded specimen, so that sections taken through the specimen will also contain a section of each of the identifying elements. Each identifying element can be a number, symbol, digit, or letter. Also such elements can be formed of a material which will accept the same stain as the specimen, so as to be more easily observable.

In addition to the elongated elements, a depth indicator may be imbedded in the embedding material. Such an indicator has a cross section, which varies as the depth of cut perpendicular to the sectioning plane, so as to indicate that level of the embedded specimen from which it was obtained.

It is an object of the present invention to provide an improved histological apparatus and article of manufacture;

It is a further object of this invention to provide means to positively identify a histological section in a convenient error-free manner;

It is still another object of the invention to provide a depth indicator for each section cut from an embedded specimen.

These and other objects of this invention will become more apparent and will be more easily understood with reference to the following detailed description taken in conjunction with the accompanying drawings, in which:

FIGS. 4a–4f are sequential diagrammatic views showing how the identifying characters are formed into a matrix and co-embedded with the specimen in a paraffin block; and FIGS. 5a–5c are front views of sections taken from various portions of the paraffin block of FIG. 1.

DETAILED DESCRIPTION OF THE INVENTION

Figure 1:
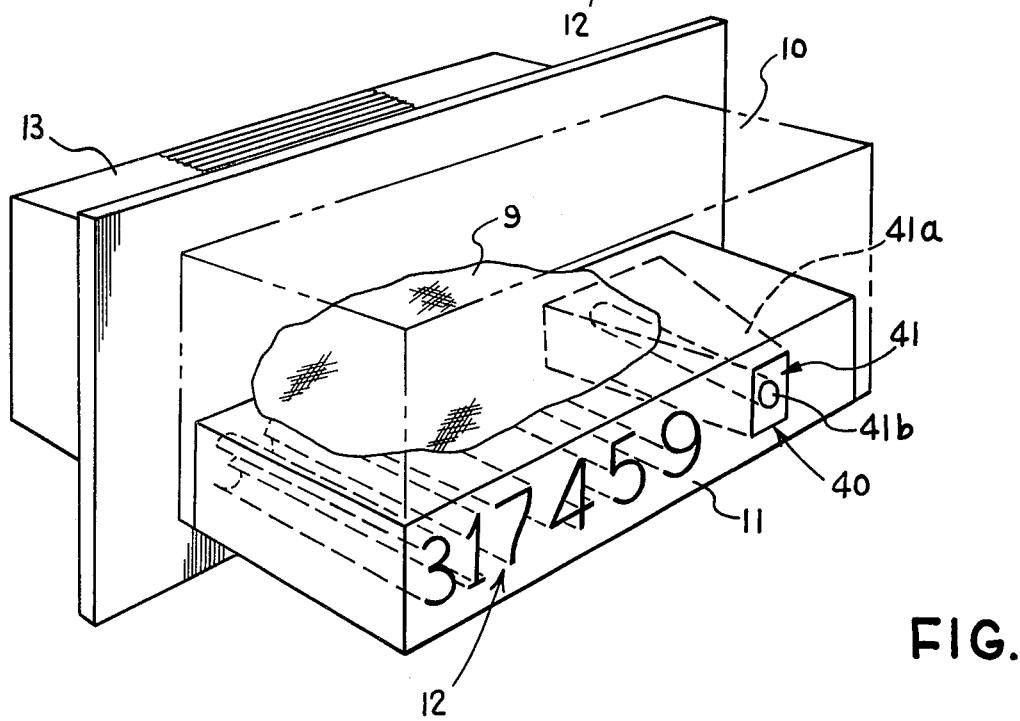
FIG. 1 is a perspective view of a paraffin block wherein a tissue specimen is co-embedded with numerical elements identifying the same.

Generally speaking, the invention contemplates numbering or otherwise labelling or identifying each section of a specimen cut from a same paraffin block. Referring to FIG. 1, a specimen 9 is embedded in a block of paraffin 10. Immediately adjacent the specimen 9 within the block 10 is located a matrix 11, comprising a plurality of elements or numbers 12 which are elongated in a direction perpendicular to the sectioning plane. The matrix 11 of numbers 12 is co-embedded with the specimen 9 within paraffin block 10. Each of the numbers 12 has a substantially constant cross section, in the plane of sectioning. The paraffin block 10 is cast by pouring hot melted paraffin into a container 30 (shown in FIG. 4e) to embed the specimen 9 and matrix 11 which have previously been infiltrated with melted paraffin. A plastic embedding ring 13 may then be placed over the block 10 and container, and a second pouring made. The block 10 is now supported by the ring 13, as shown in FIG. 1.

Figure 2:
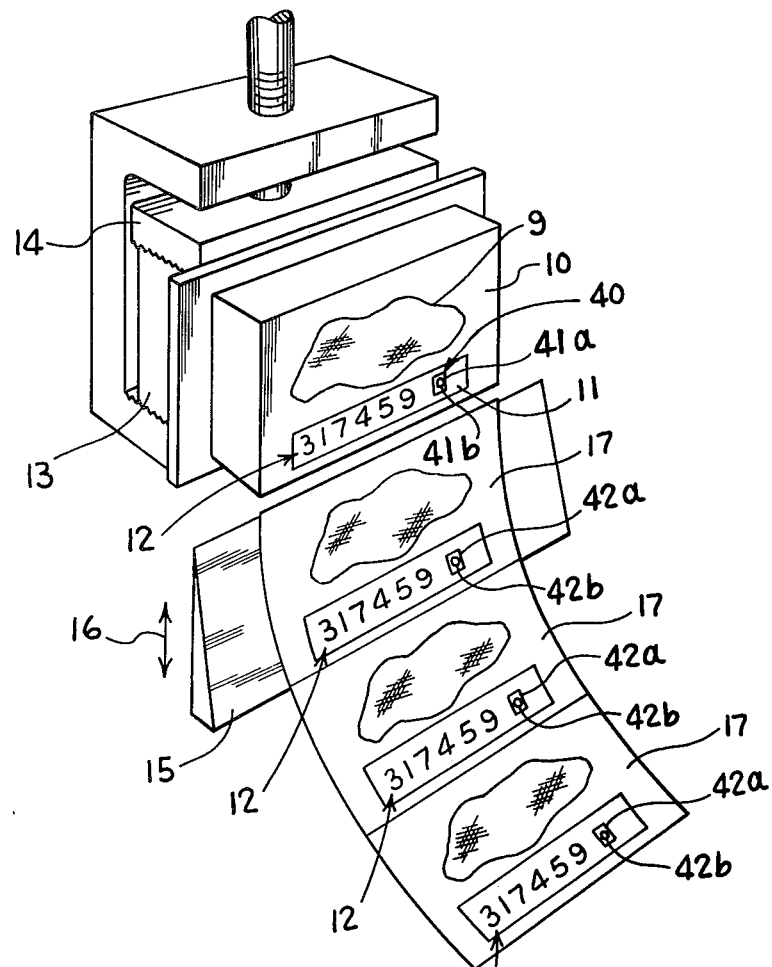
FIG. 2 is a perspective view of the paraffin block of FIG. 1 mounted in a microtome vise with a series of consecutive sections already cut from the block.

After removal of the metal container 30, the ring support 13 is placed in the vise 14 of a microtome, as illustrated in FIG. 2, where a blade 15 is caused to relatively move (arrows 16) into cutting engagement with block 10.

The blade 15 is shown after making a series of cut into block 10 to produce the thin sections 17, which will subsequently be mounted on glass slides (not shown) and stained.

As illustrated in FIG. 2, each of the sections 17 from a same block 10 has the same matrix numbers 12 and, thus, each carries the identification specific to the particular embedded specimen 9. Preferably, the elongated numbers 12 have a uniform cross section, and a length, at least, as deep as the depth of the specimen 9 in block 10. Thus, as each cut is made through the paraffin block 10, a thin section of the numbers 12 will be cut from the embedded material 11 along with a thin section of the specimen 9.

Each paraffin block casting is caused to have its own specific code or a series of numbers, so that each section of a particular specimen cannot be confused with another specimen.

This method of identification makes it unnecessary for the operator making the sections for the slides to physically mark each slide, a cumbersome and error-prone procedure.

There are many methods of producing a paraffin block 10 having a series of characters or numbers embedded alongside the specimen. This invention will detail a preferred method. However, the invention is not to be interpreted as being limited by this exemplary teaching.

Figure 3:
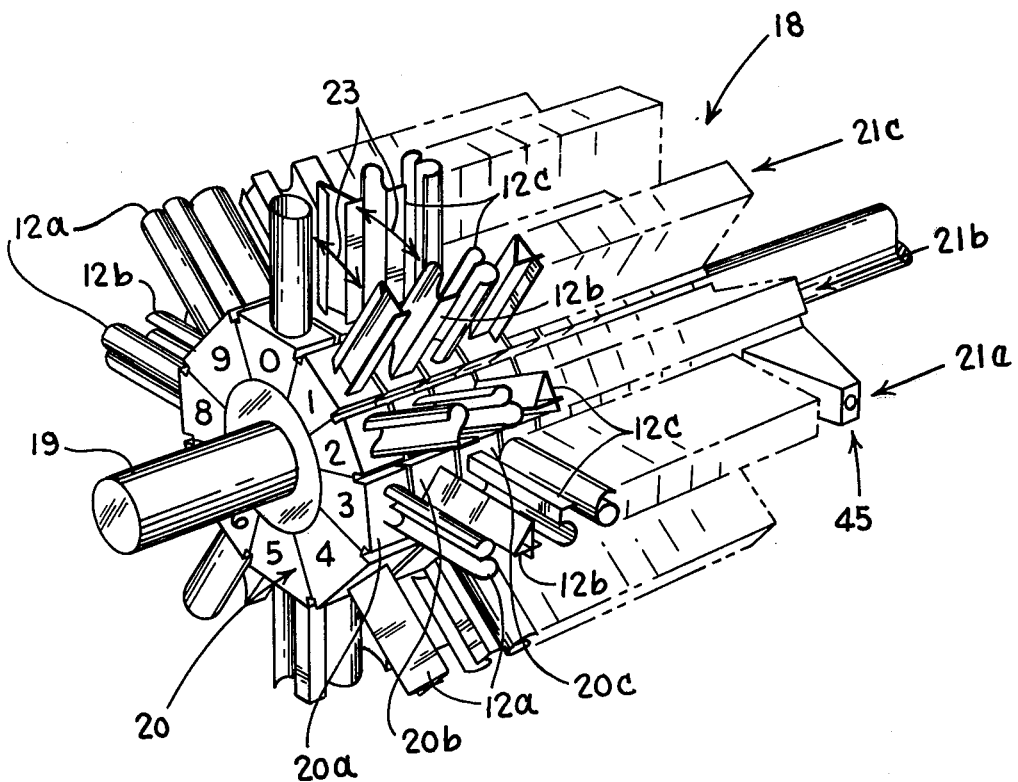
FIG. 3 is a perspective view of an encoding wheel for providing a matrix of elements for identifying each specimen.

Referring to FIGS. 3 and 4a, a numbering or encoding wheel 18 is depicted, which wheel is used in the placing of the numbers 12 within matrix 11, as illustrated in FIG. 1.

The wheel 18 comprises a shaft 19 which supports a series of contiguous discs 20. Each disc 20a, 20b, 20c, . . . etc., is free to be individually rotated (arrows 23) upon shaft 19 to any one of 10 indexed positions. Each disc 20a, 20b, 20c, etc., has a set of elongated numbers 12a, 12b, 12c, etc., radially disposed about its periphery. Each disc 20 can be indexed to a given position to produce a given sequence of numbers 12a, 12b, 12c, etc. Thus, row 21a is illustrated with a number "3456 . . . ." Naturally, it should be obvious that any number (not necessarily one having a given sequence) can be produced by the encoding wheel 18, as for example: "317459" depicted in FIG. 1.

Having chosen an appropriate number dialed into a particular row, for example, the row 21a, that row of the encoding wheel 18 is then aligned with the mouth 25 of a matrix molding pan 26, as shown in FIG. 4a. FIG. 4b depicts the row 21a of encoding wheel 18 having been lowered into the matrix pan 26. The pan 26 is now filled with a setting material which will not accept a specimen stain, such as liquified aqueous agar, and the agar is allowed to harden. After the agar has hardened, the row 21a of wheel 18 is removed from the matrix pan 26 as shown by arrow 28 in FIG. 4c. The matrix pan 26 now contains hardened agar which has a series of voids or cavities 27 disposed therein, corresponding to the numbers 12a, 12b, 12c, etc., of the row 21a of encoding wheel 18. These voids 27 are then filled with a liquified settable material, which then is permitted to set; the settable material is either already deeply and permanently colored or stained or will later accept the stain which is to be applied to specimen 9 (FIG. 1.) One such settable material which may be used for this purpose is gelatin.

After the gel has hardened, the completed matrix 11 is then lifted (arrow 29) out of pan 26, as illustrated in FIG. 4d. Matrix 11 is then placed in the container with the fresh tissue and processed through to infiltration with melted paraffin. The completed matrix 11 is oriented, as shown in FIG. 4e, in a metal pan or base mold 30 for casting with the specimen 9 to form the embedded block 10 (FIGS. 1 and 4f).

The paraffin-infiltrated specimen 9 is placed alongside the matrix 11, and the base mold 30 is then filled with liquified paraffin.

FIG. 4f shows the completed block 10 containing the specimen 9 and the matrix 11 comprising the elongated numbers 12, after removal from the mold 30.

The elongated numbers or projections 12a, 12b, 12c, etc., of wheel 18 can be made of a soft elastomer, for example, silicone rubber, to effect an easy release from the solidified agar in FIG. 4c. This is so, because the silicone rubber will stretch when the wheel 18 is pulled upward from the pan 26. The stretching of the projections 12a, 12b, 12c, etc., will cause a shrinking of the projection cross section within the agar, thus effecting a quicker release from the walls 34 of cavities 27.

The materials used to mold the matrix 11 and the numbers 12a, 12b, 12c, etc., respectively, different from each other (e.g. stainable vs. un-stainable), so that if the numbers are stained with the specimen stain, they will be readily observable within the un-stainable matrix material. The materials should also be compatible with fixing, dehydrating and embedding media and easily sectioned by the cutting blade 15 (FIG. 2).

Another desirable feature of the invention includes a depth indicator 40 (FIGS. 1,2,5a–5c) to indicate that level of specimen 9 from which the particular section (FIGS. 2, 5a–5c) was obtained. In order to determine the depth of cut of any particular section 17 in block 10, it is contemplated that a molded piece 41 (FIGS. 1 and 4f) comprising, for example, a trapazoidal wedge 41a and a cylinder 41b disposed in the middle of wedge 41a, be included in matrix 11.

The wedge 41a has a varying cross section, while the cylinder 41b has a uniform cross section, respectively, with regard to the sectioning plane (FIGS. 2, 5a–5c). Therefore, as the depth of cut becomes progressively deeper into block 10, the cross section of the sectioned portion 42a of wedge 41a will progressively change with respect to the uniform cross section of the sectioned portion 42b. FIGS. 5a, 5b and 5c illustrate three sections 17, taken from different levels of the block 10. FIG. 5a depicts a section 17 taken near the start of the sectioning procedure; FIG. 5b shows a section 17 cut from the middle of the block 10; and FIG. 5c illustrates a section 17 removed from near the end of the block 10. As can be seen from these figures, the cross section of sectioned portion 42a will continue to grow progressively larger with each succeeding cut, whereas cross section of sectioned portion 42b will stay the same with each successive cut. Therefore, a visual indication of the approximate depth of cut is provided. Relative locations of sections within the original specimen can be determined by means of this apparatus.

The indicator 40 can be molded of the same material, and in the same fashion as the numbers 12. Referring to FIG. 3, the wheel 18 can be provided with a stationary projection 45 at the end of a particular row of numbers. When the numbers are cast in pan 26 (FIGS. 4a–4d), the projection 45 is simultaneously molded into the agar to produce indicator 40.

While a definite configuration of the depth indicator 40 is shown, many other designs will naturally occur to the skilled practitioner of this art, such as two oppositely tapered cones.

Similarly, one or more of the numbers 12 may be replaced by other symbols or letters, i.e. the labels can be alpha-numeric in nature.

The wedge 41a of depth indicator 40 being molded of the same gelatin as numbers 12, will also be stained for visibility.

The numbers 12 may be constructed in various other ways such as by extrusion, dot-matrixing, etc. In addition, the numbers can be molded directly without a matrix support 11. However, the matrix 11 provides an easy way to handle or hold a long series of numbers, in proper relation to the specimen.

Having thus described the invention, what is desired to be protected by Letters Patent is presented by the following appended claims.

What is claimed is:

1. A method of labelling a histological specimen, comprising the steps of:
   (a) forming a plurality of elongated labelling elements, said labelling elements being preformed and at least the length of said specimen, said labelling elements being formed of a first material which is compatible with the subsequent fixing, dehydrating and embedding media used in the subsequent processing of said specimen and easily sectioned by a microtome,
   (b) orienting said specimen and said labelling elements within a mold in respect to a chosen sectioning plane of said specimen, said labelling elements being oriented to be at least co-extensive with portions of said specimen to be sectioned in a direction vertical to said sectioning plane,
   (c) filling said mold with an embedding medium,
   (d) allowing said embedding medium to set, and
   (e) removing said set embedding medium from said mold for subsequent positioning on a microtome for sectioning of said specimen and labelling elements.

2. The method of claim 1 wherein step (b) comprises the further step of locating said labelling elements to be spaced from said specimen within said mold.

3. The method of claim 1 wherein step (a) comprises the steps of forming a series of labelling cavities in a block of second material, and filling said cavities with said first material, each of said first and second materials being properly sliceable by a microtome.

4. The method of claim 3, comprising the further step of coloring said second material, so as to be distinguishable from said first material.

5. The method of claim 1, comprising the further step of forming said labelling elements to have a constant cross section.

6. The method of claim 1, comprising the further steps of locating a depth indicator in said mold, said depth indicator having a variable cross section in said direction vertical to said sectioning plane, said depth indicator being formed of a second material properly sliceable by a microtome, and embedding said depth indicator along with said labelling element and said specimen in said embedding medium.

7. The method of claim 6, comprising the further step of coloring said depth indicator to be distinguishable from said set embedding medium.

* * * * *